United States Patent [19]  [11] 4,018,773
Condon et al.  [45] Apr. 19, 1977

[54] PHENYLPIPERAZINOTETRAHYDRONAPH-
THOLS AND DERIVATIVES

[75] Inventors: Michael E. Condon, Lawrenceville;
Frederic P. Hauck, Somerville; Joyce Reid, Highland Park, all of N.J.

[73] Assignee: E. R. Squibb & Sons, Inc., Princeton, N.J.

[22] Filed: Sept. 15, 1975

[21] Appl. No.: 613,721

[52] U.S. Cl. .................. 260/268 PH; 260/348 A; 260/348 C; 424/250
[51] Int. Cl.² .................................. C07D 295/08
[58] Field of Search ............... 260/268 BC, 268 PH

[56] References Cited
UNITED STATES PATENTS 3,845,058 10/1974 Lembo et al. ............... 260/268 BC
3,928,358 12/1975 Renth et al. ................ 260/268 BC

*Primary Examiner*—Donald G. Daus
*Assistant Examiner*—Jose Tovar
*Attorney, Agent, or Firm*—Lawrence S. Levinson; Merle J. Smith; Donald J. Barrack

[57] ABSTRACT

Compounds having the structure

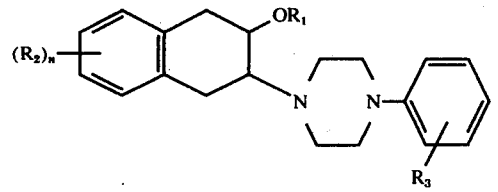

and the pharmaceutically acceptable salts thereof, wherein $R_1$ is hydrogen,

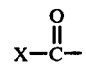

wherein X is alkyl or aryl, or

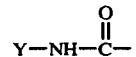

wherein Y is alkyl or aryl; $R_2$ is hydrogen, halogen, alkyl, hydroxy, alkoxy or

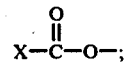

$R_3$ is hydrogen, halogen, alkyl, alkoxy, alkylthio, trifluoromethyl, or nitro; and n is 1, 2, or 3, have useful pharmacological properties.

30 Claims, No Drawings

PHENYLPIPERAZINOTETRAHYDRONAPHTHOLS AND DERIVATIVES

BRIEF DESCRIPTION OF THE INVENTION

Compounds having the structure

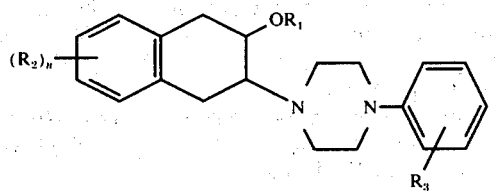

and their pharmaceutically acceptable salts, have useful pharmacological properties. In formula I and throughout the specification the symbols are as defined below:

$R_1$ is hydrogen,

wherein X is alkyl of 1 to 12 carbon atoms or aryl, or

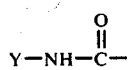

wherein Y is lower alkyl or aryl;

$R_2$ is hydrogen, lower alkyl, hydroxy, alkoxy, or

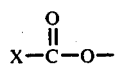

(wherein X is as defined above);

$R_3$ is hydrogen, halogen, lower alkyl, alkoxy, alkylthio, trifluoromethyl, or nitro; and n is 1, 2 or 3.

The term lower alkyl, as used throughout the specification, refers to an alkyl group having 1 to 4 carbon atoms.

The terms alkoxy and alkylthio, as used throughout the specification, refer to groups wherein the hydrocarbon portion of the group has 1 to 4 carbon atoms.

The term halogen, as used throughout the specification, refers to fluorine, chlorine, bromine and iodine; chlorine and bromine are the preferred halogens.

The term aryl, as used throughout the specification refers to phenyl, or phenyl monosubstituted with lower alkyl, alkoxy or halogen.

DETAILED DESCRIPTION OF THE INVENTION

The phenylpiperazinotetrahydronaphthols of formula I, and the pharmaceutically acceptable acid addition salts thereof, are useful as hypotensive agents in mammals, e.g., domestic animals such as dogs, cats, etc. Daily doses of from 5 to 50 mg/kg, preferably about 5 to 25 mg/kg can be administered in single or divided doses orally or by injection.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The compounds of formula I include those wherein the $-OR_1$ and phenylpiperazino groups are in the cis and in the trans configurations.

The compounds of formula I, wherein $R_1$ is hydrogen, and the $-OR_1$ and phenylpiperazino groups are in the trans configuration, can be prepared by reacting a 6,7-epoxy-5,6,7,8-tetrahydronaphthalene derivative having the formula

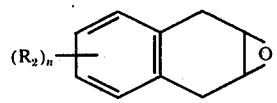

with a piperazine derivative having the formula

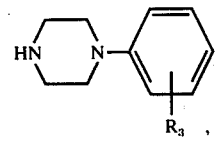

to yield a trans-phenylpiperazinotetrahydronaphthol having the formula

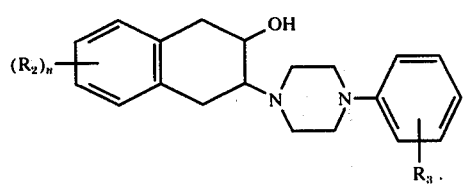

The reaction can be run in an organic solvent or in a mixture of organic solvents, preferably a mixture of an aromatic hydrocarbon and an alkanol (e.g., a mixture of xylene and methanol). Reaction conditions are not critical, but the reaction will preferably be run at the reflux temperature of the solvent.

The compounds of formula I wherein $R_1$ is hydrogen, and the $-OR_1$ and phenylpiperazino groups are in the cis configuration, can be prepared by first reacting a 6,7-epoxy-5,6,7,8-tetrahydronaphthalene of formula II with sodium azide in the presence of ammonium chloride to yield a trans compound having the formula

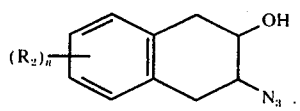

The reaction can be run in an organic solvent, preferably an ether such as 2-methoxyethanol.

Reduction of a trans compound of formula V yields the corresponding trans compound having the formula

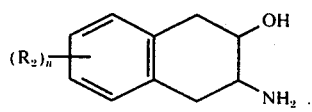

VI

The reduction reaction can be run using gaseous hydrogen and a catalyst such as platinum oxide.

Reaction of a compound of formula VI with an acyl chloride yields a trans compound having the formula

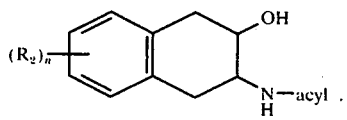

VII

The reaction can be run in an organic solvent, e.g., benzene, in the presence of alkali.

The sequential reaction of a trans compound of formula VII with thionyl chloride and a mineral acid, e.g., hydrochloric acid, yields a cis compound having the formula

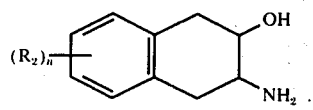

VIII

Reaction of a cis-3-amino-1,2,3,4-tetrahydro-2-naphthalenol of formula VIII with an N-(substituted phenyl)-N,N-bis-β-chloroethylamine having the formula

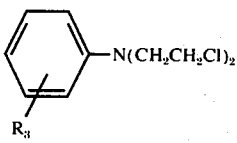

IX yields a cis-phenylpiperazinotetrahydronaphthol having the formula

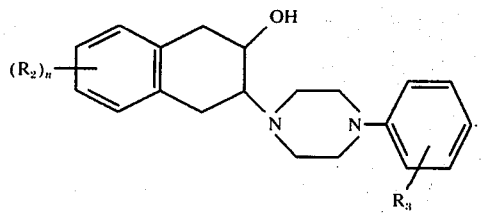

X

The reaction can be run in an organic solvent, preferably a lower alkanol, at elevated temperatures. The reaction does not go quickly, and may take up to a week to complete.

Alternatively, both cis- and trans-phenylpiperazinotetrahydronaphthols of formula I, wherein $R_1$ is hydrogen and $R_2$ is alkoxy, can be prepared from the corresponding compound of formula I wherein $R_2$ is hydroxy. The compound is reacted with a diazoalkane in an organic solvent, preferably a lower alkanol at a reduced temperature.

Reaction of a cis- or trans-phenylpiperazinotetrahydronaphthol of formula I ($R_1$ is hydrogen) with an acid anhydride having the formula

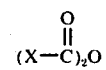

XI in the presence of an organic base, e.g., pyridine, yields the corresponding cis or trans compound having the formula

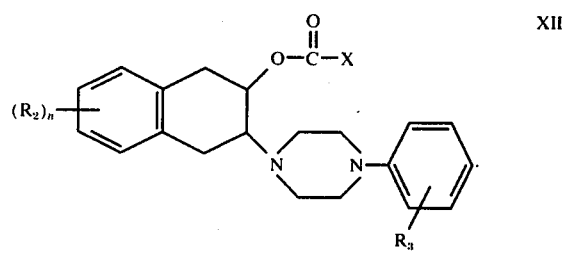

XII

Reaction of a cis- or trans-piperazinotetrahydronaphthol of formula I ($R_1$ is hydrogen) with an isocyanate having the formula

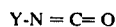

Y-N = C= O   XIII yields the corresponding cis or trans carbamate having the formula

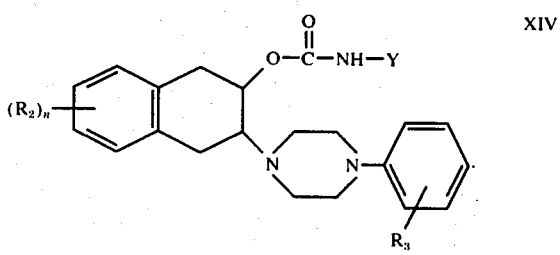

XIV

The reaction can be run in an organic solvent, preferably a polar organic solvent such as dimethylformamide or dimethylsulfoxide, in the presence of an organic base such as pyridine.

The 6,7-epoxy-5,6,7,8-tetrahydronaphthalene derivatives of formula II can be prepared from naphthalene derivatives having the structure

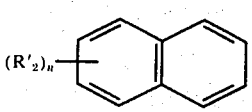

XV

In formula XV and throughout the specification, $R'_2$ can be hydrogen, halogen, lower alkyl, or hydroxy. A naphthalene derivative of formula VII can be reduced with a metal such as sodium or lithium, in liquid ammonia containing an alkanol, such as ethanol, isopropanol, t-butanol, etc. to obtain a 5,8-dihydronaphthalene derivative having the structure

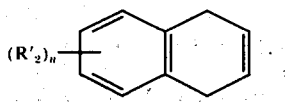

XVI

To prepare the 5,8-dihydronaphthalene derivatives necessary for the preparation of compounds of formula I wherein $R_2$ is alkoxy, the corresponding hydroxy derivative of formula XVI is reacted with an alkyl halide to yield the alkoxy-5,8-dihydronaphthalene. The reaction is carried out in a polar organic solvent, e.g., dimethylsulfoxide or dimethylformamide, in the presence of an alkali metal alkoxide, e.g., sodium methoxide or potassium ethoxide.

Reaction of a 5,8-dihydronaphthalene derivative having the structure

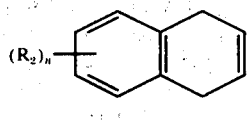

XVII with m-chloroperbenzoic acid yields a 6,7-epoxy-5,6,7,8-tetrahydronaphthalene derivative of formula II. The reaction can be carried out by mixing m-chloroperbenzoic acid with a solution of a 5,8-dihydronaphthalene derivative in an organic solvent, e.g., ethyl acetate. The resulting mixture is added to a mixture of ethyl ether and aqueous sodium bicarbonate and mixed to form the 6,7-epoxy-5,6,7,8-tetrahydronaphthalene derivative of formula II.

Alternate procedures for the preparation of the compounds of formula I will be apparent to those skilled in the art. For example, the compounds of formula I wherein $R_2$ is alkoxy can be prepared by reacting the corresponding hydroxy compounds with a diazoalkane and compounds of formula I wherein $R_2$ is

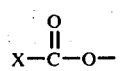

can be prepared by reacting the corresponding hydroxy compounds with an acid anhydride of formula XI.

The compounds of formula I can be utilized in the form of their pharmaceutically acceptable acid-addition salts. These salts are readily formed by methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

The following examples are specific embodiments of this invention.

EXAMPLE 1 trans-1,2,3,4-Tetrahydro-5,8-dimethoxy-3-[4-(2-methoxyphenyl)-1-piperazinyl]-2-naphthalenol A solution of 4.12 g of 6,7-epoxy-5,6,7,8-tetrahydro-1,4-dimethoxynaphthalene, 4.81 g of 1-(o-methoxyphenyl)piperazine, and 1.53 ml of isopropyl alcohol in 20 ml of xylene is refluxed under nitrogen for 19 hours. The xylene is removed in vacuo and the residue triturated with ether to give 4.01 g of crude material. Two recrystallizations of this material from ethyl acetate yield 2.5 g of the title compound, melting point 182°–183° C.

EXAMPLE 2 trans-1,2,3,4-Tetrahydro-3-(4-phenyl-1-piperazinyl)-2-naphthalenol

A solution of 7.30 g of 2,3-epoxy-1,2,3,4-tetrahydronaphthalene, 8.91 g of N-phenylpiperazine, and 19 ml of isopropanol in 50 ml of xylene is refluxed for five days. The xylene is removed in vacuo leaving a solid residue, which yields 9.9 g of crude material on trituration with isopropyl ether. Two recrystallizations from ethyl acetate yield 6.5 g of the title compound, melting point 152°–154° C.

EXAMPLE 3 trans-1,2,3,4-Tetrahydro-3-[4-(2-methoxyphenyl)-1-piperazinyl]-2-naphthalenol

A solution of 7.30 g of 2,3-epoxy-1,2,3,4-tetrahydronaphthalene, 10.56 g of 1-(o-methoxyphenyl)piperazine, and 19 ml of isopropanol in 50 ml of xylene is refluxed for five days. The xylene is removed in vacuo leaving a solid residue, which on trituration with isopropyl ether gives 11.34 g of crude material. Two recrystallizations from ethyl acetate yield 7.0 g of the title compound, melting point 159°–161° C.

EXAMPLE 4 trans-5,6,7,8-Tetrahydro-7(and 6)-[4-(2-methoxyphenyl)-1-piperazinyl]-1,6(and 1,7)-naphthalenediol A solution of 33.8 g of 6,7-epoxy-5,6,7,8-tetrahydro-1-naphthol and 42 g of 1-(o-methoxyphenyl)piperazine in 400 ml xylene is heated under reflux for 20 hours. On cooling, a large amount of solid precipitates and is removed by filtration to give 57.8 g of material. A thin layer chromatogram reveals two cleanly separated spots. This is dissolved in a hot mixture of ethyl acetate-ethanol. On cooling, crystalline material is deposited. This is recrystallized from ethyl acetate-ethanol and then from ethanol to give 7.7 g of trans-5,6,7,8-tetrahydro-6-[4-(2-methoxyphenyl)-1-piperazinyl]-1,7-naphthalenediol, melting point 199°–201° C.

The mother liquor from the harvesting above is concentrated Recrystallization from ethyl acetate give material still containing some of the slow moving isomer. This mixture (32 g) is chromatographed on 1 kg Activity III basic alumina. trans-5,6,7,8-Tetrahydro-7-[4-(2-methoxyphenyl-1-piperazinyl]-1,6-naphthalenediol (TLC pure) is eluted with chloroform. Ether is added to these fractions, and the material which crystallizes is harvested and recrystallized from ethyl acetate-methanol to yield 14.0 g of trans-5,6,7,8-tetrahydro-7-[4-(2-methoxyphenyl-1-piperazinyl]-1,6-naphthalenediol, melting point 218°–220° C.

EXAMPLE 5 trans-1,2,3,4-Tetrahydro-8-methoxy-3-[4-(2-methoxyphenyl)-1-piperazinyl]-2-naphthalenol A solution of 2.0 g of trans-5,6,7,8-Tetrahydro-6-[4-(2-methoxyphenyl)-1-piperazinyl]-1,7-naphthalenediol in methanol is treated with about 2 equivalents of freshly prepared diazomethane. The solution is stored at 0° C for 48 hours. The solvent is removed in vacuo. The residue is dissolved in ethyl acetate, washed with dilute sodium hydroxide solution and dried. The solvent is removed in vacuo leaving an oil which crystallizes on trituration with a small amount of ether. This is washed with isopropyl ether and recrystallized from ether to give 1.7 g of the title compound, melting point 123°–125° C.

EXAMPLE 6 trans-1,2,3,4-Tetrahydro-5-methoxy-3-[4-(2-methoxyphenyl)-1-piperazinyl]-2-naphthalenol A solution of 2.0 g of trans-5,6,7,8-tetrahydro-7-[4-(2-methoxyphenyl)-1-piperazinyl]-1,6-naphthalenediol in methanol is treated with about 2 equivalents of freshly prepared diazomethane. The solution is stored at 0° C for 48 hours. The solvent is removed in vacuo, the residue is dissolved in ethyl acetate and washed with dilute sodium hydroxide solution. After drying and removal of solvent in vacuo, an oil remains which crystallizes on trituration with a very small amount of ether. The crystalline material is washed with a small amount of isopropyl ether and recrystallized from ether isopropyl ether to give 1.13 g of the title compound, melting point 138°–141° C.

EXAMPLE 7 trans-1,2,3,4-Tetrahydro-3-[4-(2-methoxyphenyl)-1-piperazinyl]-2,6-(and 2,7)-naphthalenediol A mixture of 20.4 g of 6,7-epoxy-5,6,7,8-tetrahydro-2-naphthol acetate and 42.2 g of 1-(o-methoxyphenyl)-piperazine in 200 ml xylene is heated under reflux overnight. After cooling, the mixture is taken to dryness in vacuo. The material is dissolved in benzene and chromatographed on 1 kg Activity III basic alumina. After elution of fast moving material with benzene and benzene-chloroform mixture Isomer A (fractions 13–18, ~17.9g) is eluted with chloroform and Isomer B (fractions 25–34, 17.1g) is eluted with chloroform and 5% methanol is chloroform.

Fractions 14–16 (9.1g) are recrystallized from ethyl acetate-ethanol to give 5.34 g of material. This is recrystallized from a large volume (~1.5 l) of methanol to give 4.55 g of material, melting point 237°–239° C.

Ethyl acetate is added to fractions 25–31 (13.2g) and the material which crystallizes is harvested (8.64g). This is recrystallized from a large volume of methanol (~3 l) to give 6.65 of material, melting point 224°–228° C.

EXAMPLE 8 trans-5,6,7,8-Tetrahydro-7-[4-(2-methoxyphenyl)-1-piperazinyl]-1,6-naphthalenediol, diacetate ester A solution of 2.0 g of trans-5,6,7,8-tetrahydro-7-[4-(2-methoxyphenyl)-1-piperazinyl]-1,6-naphthalenediol in 20 ml of pyridine is cooled in an ice bath and treated dropwise with 2.2 ml of acetic anhydride. After standing for 2 days at room temperature the mixture is taken to near dryness in vacuo. The residue is dissolved in ethyl acetate and washed with cold dilute sodium hydroxide and twice with water. The ethyl acetate solution is dried over magnesium sulfate, filtered, and the solvent is removed in vacuo leaving 2.6 g of foam. Ether is added and the crystalline material that is deposited is harvested. This is recrystallized from ethyl acetate-isopropyl ether to give 1.88 g of the title compound, melting point 128°–132° C.

EXAMPLE 9 trans-1,2,3,4-Tetrahydro-3-(4-phenyl-1-piperazinyl)-2-naphthalenol, acetate ester A solution of 1.0 g of trans-1,2,3,4-tetrahydro-3-(4-phenyl-1-piperazinyl)-2-naphthalenol in 10 ml of pyridine is cooled in an ice bath and treated dropwise with 0.68 ml of acetic anhydride. After standing overnight at room temperature the mixture is taken to near dryness in vacuo. The residue is dissolved in ethyl acetate and washed with dilute sodium hydroxide solution and twice with water. After drying over magnesium sulfate the solvent is removed in vacuo leaving 1.18 g of viscous material. A small amount of ether is added and on standing crystalline material is deposited. This is recrystallized from isopropyl ether to give 0.9 g of the title compound, melting point 70°–75° C.

EXAMPLE 10 trans-5,6,7,8-Tetrahydro-6-[4-(2-methoxyphenyl)-1-piperazinyl]-1,7-naphthalenediol, diacetate ester A solution of 1.5 g of trans-5,6,7,8-tetrahydro-6-[4-(2-methoxyphenyl)-1-piperazinyl]-1,7-naphthalenediol in 15 ml pyridine is cooled in an ice bath and treated dropwise with 1.65 ml of acetic anhydride. The mixture is left for about 16 hours at room temperature. The mixture is taken to near dryness in vacuo. The residue is dissolved in ethyl acetate and washed with cold dilute sodium hydroxide and twice with water. After drying over magnesium sulfate, the solvent is removed in vacuo leaving 2.0 g of foam. On addition of ether-hexane the material crystallizes. This is recrystallized from ethyl acetate-hexane to give 1.6 g of the title compound, melting point 137°–141° C.

EXAMPLE 11 trans-1,2,3,4-Tetrahydro-5,8-dimethoxy-3-[4-(2-methoxyphenyl)-1-piperazinyl]-2-naphthalenol, acetate ester A solution of 920 mg of trans-1,2,3,4-tetrahydro-5,8-dimethoxy-3-[4-(2-methoxyphenyl)-1-piperazinyl]-2-naphthalenol in 10 ml pyridine is cooled in an ice bath and treated dropwise with 0.44 ml of acetic anhydride. After standing for about 1–6 hours at room temperature the mixture is taken to near dryness in vacuo. The residue is dissolved in ethyl acetate and washed with cold dilute sodium hydroxide solution and twice with water. After drying the solvent is removed in vacuo leaving 800 mg of foam. Ether is added and the material which crystallizes is recrystallized from ethyl acetate-hexane to give 0.70 g of the title compound, melting point 166°–169° C.

EXAMPLE 12 trans-1,2,3,4-Tetrahydro-6(or 7) methoxy-3-[4-(2-methoxyphenyl)1-piperazinyl]-2-naphthalenol A suspension of 1.0 g of trans-1,2,3,4-tetrahydro-3-[4-(2-methoxyphenyl)-1-piperazinyl]-2,6(or 2,7)naphthalene-diol in 100 ml methanol is cooled in an ice bath and treated with an excess of freshly prepared solution of diazomethane in ether. The mixture is left in the refrigerator for about 16 hours. The next day the yellow color is gone but a considerable amount of insoluble material remains. The mixture is stirred in an ice bath for 8 hours during which time more diazomethane solution is added. After standing 16 hours at 5° C the solution is nearly complete. After stirring with cooling for 3 additional hours a few drops of acetic acid are added to discharge the yellow color. The solvent is removed in vacuo. The residue is dissolved in ethyl acetate, washed with dilute sodium hydroxide solution and then water. After drying, the solvent is removed in vacuo to give 1.05 g of foam. This yields crystalline material on addition of ether isopropyl ether. Recrystallization from ethyl acetate-hexane yields 0.46 g of the title compound, melting point 129°–131° C.

EXAMPLE 13 trans-1,2,3,4-Tetrahydro-3-[4-(2-methoxyphenyl)-1-piperazinyl]-2,6 (or 2,7)-naphthalenediol, 2,6, (or 2,7)-diacetate trans-1,2,3,4-Tetrahydro-3-[4-(2-methoxyphenyl-1-piperazinyl]-2,6 (or 2,7)-naphthalenediol (1.0g) is partially dissolved in 10 ml of pyridine. The mixture is cooled in an ice bath and 1.1 ml acetic anhydride is added dropwise. After stiring for 1–2 hours at room temperature a clear solution is obtained. After standing for about 16 hours at room temperature the solvent is removed in vacuo. The residue is dissolved in ethyl acetate and washed with dilute sodium hydroxide solution and then twice with water. After drying, the solvent is removed in vacuo leaving a foam. Material crystallizes after the addition of hexane-ether. This is harvested and recrystallized from ether-hexane to give 0.85 g of the title compound, melting point 99°–102° C.

EXAMPLE 14 trans-1,2,3,4-Tetrahydro-3-[4-(2-methoxyphenyl)-1-piperazinyl]-2,6 (or 2,7)-naphthalenediol, diacetate trans-1,2,3,4-Tetrahydro-3-[4-(2-methoxyphenyl)-1-piperazinyl]-2,6(or 2,7)-naphthalenediol (1.0 g) is partially dissolved in 10 ml of pyridine. The mixture is cooled in an ice bath and 1.1 ml of acetic anhydride is added dropwise. After stirring a few minutes at room temperature the mixture is a clear solution which is left for about 16 hours at room temperature. The solvent was removed in vacuo, the residue is dissolved in ethyl acetate and washed with dilute sodium hydroxide solution and twice with water. After drying, the solvent is removed in vacuo leaving a foam. After standing several days is ether-hexane, crystalline material is obtained. This is recrystallized from ether-hexane to give 1.0 g of the title compound, melting point 109°–113° C.

EXAMPLE 15 trans-5,6,7,8-Tetrahydro-7-[4-(2-methoxyphenyl)-1-piperazinyl]-1,4,6-naphthalenetriol A solution of 13.1 g of 6,7-epoxy-5,6,7,8-tetrahydro-1,4-diacetoxynaphthalene and 29.8 g of 1-(o-methoxyphenyl)piperazine in 200 ml of xylene is refluxed under nitrogen for 48 hours. The reaction mixture is then cooled, the crystalline precipitate filtered, washed with ether, and dried in vacuo to afford 10.55 g of crude crystalline product. Recrystallization of 7.50 g of this material from ethyl acetate/ethanol gives 4.0 g of the title compound, melting point 222°–224° C.

EXAMPLE 16 trans-1,2,3,4-Tetrahydro-6(or 7)-methoxy-3-[4-(2-methoxyphenyl)-1-piperazinyl]-2-naphthalenol A suspension of 1.0 g of trans-1,2,3,4-tetrahydro-3-[4-(2-methoxyphenyl)-1-piperazinyl]-2,6 (or 2,7)-naphthalene-diol in 100 ml methanol is cooled in an ice bath and treated with an excess of a freshly prepared solution of diazomethane in ether. After standing for about 16 hours in a refrigerator the yellow color is gone but a considerable amount of insoluble material remains. More diazomethane solution is added (in 3 portions) and the mixture is stirred for about 8 hours while cooling in an ice bath. After standing in a refrigerator for about 16 hours, the addition of more diazomethane and stirring is repeated. The third day the mixture is just stirred. After standing in the cold for about 16 hours again nearly all the solid is gone. A few drops of glacial acetic acid are added to discharge yellow color. The mixture is taken to dryness in vacuo. The residue is dissolved in warm ethyl acetate and washed with dilute sodium hydroxide solution and then with water. After drying, the solvent is removed in vacuo to give 1.05 g of partially crystalline material. Ether is added and crystalline material is harvested. Recrystallization from ethyl acetate-hexane gives 0.79 g of the title compound, melting point 148°–150° C.

EXAMPLE 17 trans-5,6,7,8-Tetrahydro-7-[4-(2-methoxyphenyl)-1-piperazinyl]-1,4,6-naphthalenetriol, triacetate ester A solution of 3.0 g of trans-5,6,7,8-tetrahydro-7-[4-(2-methoxyphenyl)-1-piperazinyl]-1,4,6-naphthalenetriol in 75 ml of pyridine and 25 ml of acetic anhydride is stored at room temperature overnight. The solution is concentrated in vacuo, the residue taken up in ether, washed with cold dilute sodium hydroxide, saturated sodium chloride, dried, and concentrated in vacuo to an oil. Trituration with isopropyl ether gives 3.7 g of crude solid product. Two recrystallization from ethyl acetate/hexane give 1.4 g of the title compound, melting point 168–170° C.

EXAMPLE 18 trans-1,2,3,4-Tetrahydro-5,8-dimethoxy-3-[4-(2-methoxyphenyl)-1-piperazinyl]-2-naphthalenol, propanoate ester trans-1,2,3,4-Tetrahydro-5,8-dimethoxy-3-[4-(2-methoxyphenyl)-1-piperazinyl]-2-naphthalenol (6.0 g) is partially dissolved in 70 ml of pyridine. The mixture is cooled in an ice bath and treated dropwise with 3.9 ml of propionic anhydride. The mixture is clear after stirring at room temperature for 44 hours. After taking to dryness in vacuo, the residue is dissolved in ethyl acetate and washed twice with cold dilute sodium hydroxide solution and twice with saturated sodium chloride solution. After drying, the solvent is removed in vacuo leaving 7.35 g of foam. This is dissolved in ether. On standing 4.3 g of crystalline material is deposited. This is recrystallized from ether to give 2.9 g of the title compound, melting point 100°–105° C.

EXAMPLE 19 trans-1,2,3,4-Tetrahydro-5,8-dimethoxy-3-[4-(2-methoxyphenyl)-1-piperazinyl]-2-naphthalenol, butanoate ester trans-1,2,3,4-Tetrahydro-5,8-dimethoxy-3-[4-(2-methoxyphenyl)-1-piperazinyl]-2-naphthalenol (6.0 g) is partially dissolved in 70 ml of pyridine. The mixture is cooled in an ice bath and treated dropwise with 4.75 ml of butyric anhydride. After stirring for 2 days at room temperature the clear solution is taken to dryness in vacuo. The residue is dissolved in ethyl acetate and washed twice with cold dilute sodium hydroxide solution and twice with saturated sodium chloride solution. After drying, the solvent is removed in vacuo leaving 7.35 g of foam. This is dissolved is isopropyl ether and after standing several days in the freezer, crystalline material is deposited. This is recrystallized from ether-hexane with a charcoal decolorization to give 2.75 g of the title compound, melting point 73°–78° C.

EXAMPLE 20 trans-1,2,3,4-Tetrahydro-5,6,8 (and 5,7,8)-trimethoxy-3-[4-(2-methoxyphenyl)-1-piperazinyl]-2-naphthalenol A solution of 3.4 g of 1,2,4-trimethoxy-6,7-epoxy-5,6,7,8-tetrahydronaphthalene, 2.8 g of 1-(o-methoxyphenyl)piperazine, and 3.1 ml of isopropanol in 30 ml of xylene is heated under reflux for 5 days. After cooling the mixture is taken to near dryness in vacuo. The residue contains some solids. Isopropyl ether is added and 2.6 g of solid is harvested. This is recrystallized from ethyl acetate with a charcoal decolorization to give 1.25 g of the title compound, melting point 210°–213° C.

The mother liquor from the above crystallization of crude material is taken to dryness and the 4.8 residue is dissolved in benzene and chromatographed on a 120 g column of basic alimina (Activity III). After elution of the faster moving isomer with benzene, the other isomer is eluted with benzene and 30% ethyl acetate in benzene. Isopropyl ether is added to fractions containing the second isomer to give 1.1 g of crystalline material. This is recrystallized from ethyl acetate to give 0.6 g of the title compound, melting point 167°–170° C.

EXAMPLE 21 trans-1,2,3,4-Tetrahydro-6,7-dimethoxy-3-[4-(2-methoxyphenyl)-1-piperazinyl]-2 -naphthalenol

A solution of 2.94 g of 2,3-dimethoxy-6,7-epoxy-5,6,7,8-tetrahydronaphthalene, 2.9 g of 1-(o-methoxyphenyl)piperazine, and 1 ml of isopropanol in 30 ml of xylene is refluxed for 5 days. The reaction mixture is concentrated in vacuo, the residue taken up in ethyl acetate, and this is thoroughly extracted with dilute hydrochloric acid. The combined acid extracts are made basic with dilute sodium hydroxide solution, and this is thoroughly extracted with ethyl acetate. The combined ethyl acetate extracts are dried and concentrated in vacuo to an oil, which gives 1.3 g of solid on trituration with ethyl acetate. Recrystallization from ethyl acetate gives 600 mg of the title compound, melting point 172°–174° C.

EXAMPLE 22 trans-3-[4-(2-Chlorophenyl)-1-piperazinyl]-1,2,3,4-tetrahydro-5,8-dimethoxy-2-naphthalenol A solution of 10.3 g of 2,3-epoxy-5,8-dimethoxy-1,2,3,4-tetrahydronaphthalene, 9.83 g of o-chlorophenylpiperazine and 2 ml of absolute ethanol in 100 ml xylene is refluxed for 5 days. The solution is then concentrated in vacuo, and the residue is triturated with ether to give 12.0 g of crude product. Recrystallization from ethanol/methanol gives the title compound, melting point 237°–239° C.

EXAMPLE 23 trans-1,2,3,4-Tetrahydro-5,8-dimethoxy-3-[4-(2-methylphenyl)-1-piperazinyl]-2-naphthalenol A solution of 10.3 g of 2,3-epoxy-5,8-dimethoxy-1,2,3,4-tetrahydronaphthalene, 8.8 g of o-tolylpiperazine, and 2 ml of absolute ethanol in 100 ml of xylene is refluxed for 4 days. The reaction mixture is cooled to room temperature, and the resulting crystalline solid filtered off and washed with ether to give 15.2 g of crude product. Recrystallization from ethanol/methanol gives 4 g of the title compound, melting point 217°–219° C.

EXAMPLE 24 trans-1,2,3,4-Tetrahydro-5,8-dimethoxy-3-[4-[3-(trifluoromethyl)phenyl]-1-piperazinyl]-2-naphthalenol A solution of 10.3 g of 2,3-epoxy-5,8-dimethoxy-1,2,3,4-tetrahydronaphthalene, 11.5 g of N-($\alpha,\alpha,\alpha$-trifluoro-m-tolyl)piperazine, and 2 ml of absolute ethanol in 100 ml of xylene is refluxed for 7 days. The reaction mixture is concentrated in vacuo, and the residue is triturated with ether to give 11.9 g of crude product. Recrystallization from ethyl acetate gives 8.0 g of the title compound, melting point 184°–187° C.

EXAMPLE 25 trans-3-[4-[2-(Ethylthio)phenyl]-1-piperazinyl]-1,2,3,4-tetrahydro-5,8-dimethoxy-2-naphthalenol A solution of 10.3 g of 6,7-epoxy-5,6,7,8-tetrahydro-1,4-dimethoxynaphthalene, 11.9 g of 1-o-ethylmercaptophenylpiperazine, and 2 ml isopropanol in 100 ml of xylene is heated under reflux for 6 days. The solution is taken to dryness in vacuo leaving partially crystalline material. After trituration with isopropyl ether the crystalline material is harvested by filtration. Two recrystallizations from ethyl acetate give 9.45 g of the title compound, melting point 171°–173° C.

EXAMPLE 26 trans-1,2,3,4-Tetrahydro-5,8-dimethoxy-3-[4-(2-methoxyphenyl)-1-piperazinyl]-2-naphthalenol, butylcarbamate To a suspension of 3.98 g of trans-1,2,3,4-tetrahydro-5,8-dimethoxy-3-[4-(2-methoxyphenyl)-1-piperazinyl]-2-naphthalenol in 20 ml of N,N-dimethylformamide and 15 ml of pyridine is added 2 ml of n-butyl isocyanante, and the resulting mixture is stirred and heated at 100° C for 6 hours. The resulting clear solution is concentrated in vacuo and the residue is triturated with diisopropyl ether to give 3.5 g of crude product. Two recrystallizations from diisopropyl ether give 1.5 g of the title compound, melting point 105°–108° C.

EXAMPLE 27 cis-1,2,3,4-Tetrahydro-5,8-dimethoxy-3-[4-(2-methoxyphenyl)-1-piperazinyl]-2-naphthalenol A. trans-3-Triazo-1,2,3,4-tetrahydro-5,8-dimethoxy-2-naphthalenol A mixture of 12.36 g of 6,7-epoxy-5,6,7,8-tetrahydro-1,4-dimethoxynaphthalene, 15.6 g of sodium azide, and 3.48 g of ammonium chloride in 162 ml 2-methoxyethanol and 24 ml water is stirred in a bath maintained at 80° C+5° for 18 hours. The mixture is taken to dryness in vacuo. The solid is partially dissolved in water, some sodium chloride is added, and the product is extracted into chloroform, dried and freed of solvent in vacuo to give 15.2 g of solid azide.

B. trans-3-Amino-1,2,3,4-tetrahydro-5,8-dimethoxy-2-naphthalenol

The crude azide is dissolved in 200 ml of absolute ethanol, treated with 0.8 g of platinum oxide, and hydrogenated on a Parr shaker for 24 hours. The bottle is vented and refilled with hydrogen every 15 minutes for the first hour, then once an hour for 6 hours before the mixture is left shaking for 16 hours. After heating to dissolve precipitated material, the catalyst is removed by filtration and washed with hot ethanol. The filtrate is taken to dryness in vacuo leaving a waxy solid. This is triturated with ethyl acetate/ether to give 11.5 g of solid amine.

C. trans-3-Amino-1,2,3,4-tetrahydro-5,8dimethoxy-2-naphthalenol, hydrochloride (1:1)

A solution of 3.7 g of trans-3-amino-1,2,3,4-tetrahydro-5,8-dimethoxy-2-naphthalenol is isopropanol is converted to the hydrochloride salt by adding a solution of hydrogen chloride in isopropanol. The salt is precipitated by adding ether and recrystallized twice from isopropanol to give 1.3 g of the title compound, melting point 213°–216° C.

D. trans-3-Benzamido-1,2,3,4-tetrahydro-5,8-dimethoxy-2-naphthalenol

A solution of 74.8 g of trans-3-amino-1,2,3,4-tetrahydro-5,8-dimethoxy-2-naphthalenol, hydrochloride in 2 liters of water is cooled in an ice bath and a solution of 40 g of benzoyl chloride in 300 ml of benzene is added. While stirring vigorously a solution of 23 g of sodium hydroxide in 100 ml of water is added dropwise at 0°–5° C over a period of 30 minutes. Semi-solid material begins adhering to the sides of the flask almost immediately. The mixture is stirred at 0°–5° C for an additional 2 hours. The solid is removed by filtration, washed with a small amount of water, then washed with chloroform and dried in vacuo over phosphorous pentoxide to give 78.5 g of the title compound.

E. cis-3-Amino-1,2,3,4-tetrahydro-5,8-dimethoxy-2-naphthalenol

The crude benzamido compound (78.5 g) is added in several portions to 180 ml of cold thionyl chloride. After the addition is complete the mixture is stired at room temperature for 45 minutes and then heated at 50° C for 2½ hours. The thionyl chloride is removed in vacuo, and the residue is treated with 700 ml of 10% hydrochloric acid and heated under reflux for about 16 hours. Charcoal is added to the hot solution and this is filtered through a pad. On cooling, benzoic acid crystallizes from the filtrate and is removed by filtration. This filtrate is taken to near dryness in vacuo leaving very viscous material. This is dissolved in ethanol-methanol and again taken to dryness in vacuo leaving a waxy solid. The crude hydrochloride is dissolved in 200 ml water. This is extracted exhaustedly with ethyl acetate, and the aqueous layer is then made alkaline with sodium hydroxide. The solid free base is harvested by filtration, washes with water and dried in vacuo to give 21.5 g of product. A 2.0 g sample of this is recrystallized from isopropanol with a charcoal decolorization to give 1.1 g of the title compound, melting point 193°–196° C.

F. cis-1,2,3,4-Tetrahydro-5,8-dimethoxy-3-[4-(2-methoxyphenyl)-1-piperazinyl]-2-naphthalenol A solution of 2.23 g of cis-3-amino-1,2,3,4-tetrahydro-5,8-dimethoxy-2-naphthalenol and 2.48 g of N-(o-methoxyphenyl)-N,N-bis-β-chloroethylamine in 25 ml of n-butanol is heated in a small Parr bomb at 140°–150° C for 5 days. The cooled solution is taken to dryness in vacuo and the residue is diluted with water and made basic with dilute aqueous sodium hydroxide. This is thoroughly extracted with ethyl acetate, and the combined extracts are washed with saturated aqueous sodium chloride, dried, and concentrated in vacuo to give 3.5 g of a semi-solid material. Trituration with ether yields 1.5 g of crude product.

A sample (2.6 g) of the above crude product is dissolved in chloroform and applied to an alumina column (75 g of Activity III, basic). Elution with chloroform (20 ml fractions) gives (fractions 3–5) 1.5 g of solid. Direct recrystallization of this material from ethyl acetate/methanol with charcoal decolorizations gives the analytical sample (0.92 g) melting point 198°–199° C.

EXAMPLE 28 trans-1,2,3,4-Tetrahydro-3-(4-phenyl-1-piperazino)-2-naphthalenol, benzoate ester Following the procedure of Example 9, but substituting benzoic anhydride for acetic anhydride, yields trans-1,2,3,4-tetrahydro-3-(4-phenyl-1-piperazino)-2-naphthalenol, benzoate ester.

EXAMPLE 29 trans-1,2,3,4-Tetrahydro-5,8-dimethoxy-3-[4-(2-methoxyphenyl)-1-piperazino]-2-naphthalenol, phenylcarbamate Following the procedure of Example 26, but substituting phenyl isocyanate for n-butyl isocyanate, yields trans-1,2,3,4-tetrahydro-5,8-dimethoxy-3-[4-(2-methoxyphenyl)-1-piperazino]-2-naphthalenol, phenylcarbamate.

EXAMPLE 30 trans-1,2,3,4-Tetrahydro-5,8-dichloro-3-[4-(2-methoxyphenyl)-1-piperazino]-2-naphthalenol Following the procedure of Example 1, but substituting 6,7-epoxy-5,6,7,8-tetrahydro-1,4-dichloronaphthalene for 6,7-epoxy-5,6,7,8-tetrahydro-1,4-dimethoxynaphthalene yields trans-1,2,3,4-tetrahydro-5,8-dichloro-3-[4-(2-methoxyphenyl)-1-piperazino]-2-naphthalenol.

EXAMPLE 31 trans-1,2,3,4-Tetrahydro-5,8-dimethyl-3-[4-(2-methoxyphenyl)-1-piperazino]-2-naphthalenol Following the procedure of Example 1, but substituting 6,7-epoxy-5,6,7,8-tetrahydro-1,4-dimethylnaphthalene for 6,7-epoxy-5,6,7,8-tetrahydro-1,4-dimethoxynaphthalene yields trans-1,2,3,4-tetrahydro-5,8-dimethyl-3-[4-(2-methoxyphenyl)-1-piperazino]-2-naphthalenol.

What is claimed is:

1. A compound having the formula

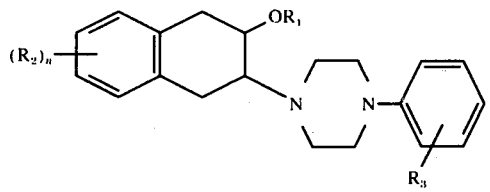

or a pharmaceutically acceptable salt thereof, wherein $R_1$ is hydrogen; $R_2$ is hydrogen, halogen, lower alkyl, hydroxy, or alkoxy; $R_3$ is hydrogen; halogen, lower alkyl, alkoxy, alkylthio, trifluoromethyl or nitro; and $n$ is 1, 2 or 3; wherein the terms lower alkyl, alkoxy, and alkylthio refer to groups having 1 to 4 carbon atoms.

2. A compound in accordance with claim 1 wherein the $OR_1$ group and the phenylpiperazino group are in the cis configuration.

3. A compound in accordance with claim 1 wherein the $OR_1$ group and the phenylpiperazino group are in the trans configuration.

4. A compound in accordance with claim 1 wherein $R_2$ is hydrogen, hydroxy or alkoxy.

5. A compound in accordance with claim 1 wherein $R_2$ is alkoxy.

6. A compound in accordance with claim 1 wherein $R_2$ is hydrogen.

7. A compound in accordance with claim 1 wherein $R_3$ is hydrogen.

8. A compound in accordance with claim 1 wherein $R_3$ is alkoxy.

9. A compound in accordance with claim 1 wherein $n$ is 1 or 2.

10. A compound in accordance with claim 1 wherein $R_2$ and $R_3$ are each methoxy.

11. The compound in accordance with claim 1 having the name trans-1,2,3,4-tetrahydro-5,8-dimethoxy-3-[4-(2-methoxyphenyl)-1-piperazinyl]-2-naphthalenol.

12. The compound in accordance with claim 1 having the name trans-1,2,3,4-tetrahydro-3-(4-phenyl-1-piperazinyl)-2-naphthalenol.

13. The compound in accordance with claim 1 having the name trans-1,2,3,4-tetrahydro-3-[4-(2-methoxyphenyl)-1-piperazinyl]-2-naphthalenol.

14. The compound in accordance with claim 1 having the name trans-5,6,7,8-tetrahydro-7-[4-(2-methoxyphenyl)-1-piperazinyl]-1,6-naphthalenediol.

15. The compound in accordance with claim 1 having the name trans-5,6,7,8-tetrahydro-6-[4-(2-methoxyphenyl)-1-piperazinyl]-1,7-naphthalenediol.

16. The compound in accordance with claim 1 having the name trans-1,2,3,4-tetrahydro-8-methoxy-3-[4-(2-methoxyphenyl)-1-piperazinyl]-2-naphthalenol.

17. The compound in accordance with claim 1 having the name trans-1,2,3,4-tetrahydro-5-methoxy-3-[4-(2-methoxyphenyl)-1-piperazinyl]-2-naphthalenol.

18. The compound in accordance with claim 1 having the name trans-1,2,3,4-tetrahydro-3-[4-(2-methoxyphenyl)-1-piperazinyl]-2,6-naphthalenediol.

19. The compound in accordance with claim 1 having the name trans-1,2,3,4-tetrahydro-3-[4-(2-methoxyphenyl)-1-piperazinyl]-2,7-naphthalenediol.

20. The compound in accordance with claim 1 having the name trans-1,2,3,4-tetrahydro-6-methoxy-3-[4-(2-methoxyphenyl)-1-piperazinyl]-2-naphthalenol.

21. The compound in accordance with claim 1 having the name trans-1,2,3,4-tetrahydro-7-methoxy-3-[4-(2-methoxyphenyl)-1-piperazinyl]-2-naphthalenol.

22. The compound in accordance with claim 1 having the name trans-5,6,7,8-tetrahydro-7-[4-(2-methoxyphenyl)-1-piperazinyl]-1,4,6-naphthalenetriol.

23. The compound in accordance with claim 1 having the name trans-1,2,3,4-tetrahydro-5,6,8-trimethoxy-3-[4-(2-methoxyphenyl)-1-piperazinyl]-2-naphthalenol.

24. The compound in accordance with claim 1 having the name trans-1,2,3,4-tetrahydro-5,7,8-trimethoxy-3-[4-(2-methoxyphenyl)-1-piperazinyl]-2-naphthalenol.

25. The compound in accordance with claim 1 having the name trans-1,2,3,4-tetrahydro-6,7-dimethoxy-3-[4-(2-methoxyphenyl)-1-piperazinyl]-2-naphthalenol.

26. The compound in accordance with claim 1 having the name trans-3-[4-(2-chlorophenyl)-1-piperazinyl]-1,2,3,4-tetrahydro-5,8-dimethoxy-2-naphthalenol.

27. The compound in accordance with claim 1 having the name trans-1,2,3,4-tetrahydro-5,8-dimethoxy-3-[4-(2 methylphenyl)-1-piperazinyl]-2-naphthalenol.

28. The compound in accordance with claim 1 having the name trans-1,2,3,4-tetrahydro-5,8-dimethoxy-3-[4-[3-(trifluoromethyl)phenyl]-1-piperazinyl]-2-naphthalenol.

29. The compound in accordance with claim 1 having the name trans-3-[4-[2-(ethylthio)phenyl]-1-piperazinyl]-1,2,3,4-tetrahydro-5,8-dimethoxy-2-naphthalenol.

30. The compound in accordance with claim 1 having the name cis-1,2,3,4-tetrahydro-5,8-dimethoxy-3-[4-(2-methoxyphenyl)-1-piperazinyl]-2-naphthalenol.

* * * * *

UNITED STATES PATENT AND TRADEMARK OFFICE
CERTIFICATE OF CORRECTION

PATENT NO. : 4,018,773
DATED : April 19, 1977
INVENTOR(S) : Michael E. Condon et al.

It is certified that error appears in the above-identified patent and that said Letters Patent are hereby corrected as shown below:

Column I, line 35, insert the word "halogen," after the word "hydrogen,".

Column I, line 45, the words "lower alkyl" should be in quotes.

Column I, line 48, the words "alkoxy" and "alkylthio" should be in quotes.

Column I, line 51, the word "halogen" should be in quotes.

Column I, line 54, the word "aryl" should be in quotes.

Column 6, line 50, "Recrystallization" should read -- Recrystallizations --

Column 6, line 54, "[4-(2-methoxyphenyl-1-" should read -- [4-(2-methoxyphenyl)-1- --.

Column 6, line 59, "(2-methoxyphenyl-1-" should read -- (2-methoxyphenyl)-1- --.

Column 7, line 42, "is" should read -- in --.

Column 11, line 40, "4.8" should read -- 4.8g --.

UNITED STATES PATENT OFFICE
CERTIFICATE OF CORRECTION

Patent No. 4,018,773　　　　　　　　　Dated April 19, 1977

Inventor(s) Michael E. Condon et al.

It is certified that error appears in the above-identified patent and that said Letters Patent are hereby corrected as shown below:

Column 13, line 58, "stired" should read -- stirred --.

Signed and Sealed this twelfth Day of July 1977

[SEAL]

Attest:

RUTH C. MASON
Attesting Officer

C. MARSHALL DANN
Commissioner of Patents and Trademarks